United States Patent [19]

Richmond

[11] Patent Number: 5,445,630

[45] Date of Patent: Aug. 29, 1995

[54] SPIKE WITH LUER FITTING

[76] Inventor: Frank M. Richmond, 205 A Grant St., Harvard, Ill. 60033

[21] Appl. No.: 98,629

[22] Filed: Jul. 28, 1993

[51] Int. Cl.⁶ .................................. A61B 19/00
[52] U.S. Cl. ...................... 604/411; 604/403; 604/414; 604/905; 604/280; 604/283
[58] Field of Search ............... 128/912, D26; 604/56, 604/82–92, 148, 161, 200–205, 213, 240–247, 249, 256, 259, 323, 403, 411, 414, 415, 905, 167, 169, 244, 245, 257, 280, 283, 284

[56] References Cited

U.S. PATENT DOCUMENTS

| | | |
|---|---|---|
| 4,059,109 | 11/1977 | Tischlinger . |
| 4,311,137 | 1/1982 | Gerard .................... 604/284 |
| 4,387,879 | 6/1983 | Tauschinski .............. 604/249 |
| 4,614,437 | 9/1986 | Buehler . |
| 4,683,916 | 8/1987 | Raines . |
| 4,842,591 | 6/1989 | Luther ..................... 604/283 |
| 4,917,668 | 4/1990 | Haindl ..................... 604/167 |
| 5,071,413 | 12/1991 | Utterberg ................. 604/905 |
| 5,085,645 | 2/1992 | Purdy et al. .............. 604/256 |
| 5,232,109 | 8/1993 | Tirrell et al. ............. 604/415 |
| 5,242,393 | 9/1993 | Brimhall et al. .......... 604/249 |
| 5,251,873 | 10/1993 | Atkinson et al. .......... 604/256 |
| 5,269,771 | 12/1993 | Thomas et al. ............ 604/256 |
| 5,295,657 | 3/1994 | Atkinson ................... 604/256 |

Primary Examiner—Randall L. Green
Assistant Examiner—P. Zuttarelli
Attorney, Agent, or Firm—John L. Rogitz

[57] ABSTRACT

A hollow spike has a pointed distal end, a proximal end, and a luer fitting positioned in the proximal end of the spike to engage a complementary fitting associated with another IV component, e.g., an IV line. A reflex valve is disposed in the luer fitting to permit fluid flow through the spike when a complementary fitting is connected to the luer fitting of the spike, and to prevent fluid flow through the spike when no fitting is engaged with the fitting of the spike.

24 Claims, 3 Drawing Sheets

SPIKE WITH LUER FITTING

FIELD OF THE INVENTION

The present invention relates generally to IV set components, and more particularly to spikes for puncturing membranes of IV fluid bags and bottles.

BACKGROUND

One of the most widely used methods of medical therapy is the intravenous (IV) infusion of liquid medicaments and/or nutrients into the bloodstream of a patient. A familiar apparatus that is used in many IV infusion applications is an IV container, such as an IV bag or bottle, which contains the liquid to be infused into the patient.

When the IV container is a bag, a rigid, hollow, sharpened IV spike is pushed into the bag to establish a pathway for fluid communication through which the liquid can flow out of the bag. The spike is usually inserted into the bag through a sealed membrane, commonly referred to as a port. In turn, the spike is connected to or formed integrally with an inlet port of a small, elongated, transparent hollow container familiarly referred to as a "drip chamber", with the fluid pathway of the spike in fluid communication with the inlet port of the drip chamber. Alternatively, the spike can be connected directly to an IV line to establish a pathway for fluid communication from the IV bag to the IV line. In either case, it is to be appreciated that once the spike has punctured the bag, fluid flow through the spike cannot be stopped in the event that the component to which the spike is connected must be removed from the IV set. This effectively limits modification of the IV set architecture once the spike is in place.

In my U.S. Pat. No. 5,391,150 for an invention entitled "IV BAG WITH NEEDLELESS CONNECTOR", Ser. No. 08/123,632, filed Sep. 16, 1993 for an invention entitled "LIQUID MEDICAMENT BAG WITH NEEDLELESS CONNECTOR FITTING USING BOAT ASSEMBLY", and Ser. No. 08/098,499, filed Jul. 28, 1993 for an invention entitled "DRIP CHAMBER WITH LUER FITTING", I have disclosed various needleless IV set components/including IV bags, cell culture bags configured essentially as IV bags, and IV drip chambers, which incorporate reflex valves and luer fittings to permit the easy and virtually drip-free assembly and/or modification of IV sets according to user-determined architectures, without requiring the use of sharp connectors, colloquially known as "sharps". By avoiding the use of sharps, my needleless components can help reduce the liklihood of medical personnel spreading blood diseases by inadvertently puncturing themselves with the sharps, and can help prevent damage to certain containers, e.g., IV bags, by minimizing the use of sharps.

As recognized by the present invention, however, many IV bags will continue to be manufactured with ports that have puncturable membranes, and that consequently require the use of spikes to establish a pathway for fluid flow out of the bag. Accordingly, the present invention recognizes that it would be advantageous to provide a spike which is compatible with other needleless IV set components.

Accordingly, it is an object of the present invention to provide a spike which does not require the use of "sharps" in infusing or extract fluid from the bag. Another object of the present invention to provide a spike which is easy to use and cost-effective to manufacture. A further object of the present invention is to provide a valve apparatus in an IV spike for engaging a complementary fitting, without the need to use a sharp connector and without requiring that the bag to which the spike is connected be empty of fluid, e.g., cell culture fluid.

SUMMARY OF THE INVENTION

A spike is disclosed for puncturing the membrane of a fluid bag, e.g., an intravenous (IV) bag or bottle. The spike includes a hollow puncturing element which has a pointed distal end configured for puncturing the membrane of the bag and an open proximal end, and the open proximal end is configured as a first luer fitting for engaging a complementarily-shaped second luer fitting. A valve is disposed in the proximal end of the puncturing element, with the valve having an open configuration, wherein a pathway for fluid communication is established through the spike when the second luer fitting is engaged with the first, and a closed configuration, wherein a pathway for fluid communication is not established through the spike when the second luer fitting is not engaged with the first. Further, the spike can have an additional pathway for fluid communication to configure the spike as a vented spike.

As intended by the present invention, the luer fitting of the spike can be a female luer fitting or a male luer fitting. When the spike has a male luer fitting, an annular cap is engaged with the male luer fitting in a surrounding relationship with the fitting. The cap has a threaded inner surface facing the male luer fitting and spaced therefrom for threadably engaging a complementarily threaded surface. If desired, the cap can be rotatably engaged with the male luer fitting, or can be fixedly attached to the male luer fitting.

In accordance with the present invention, the valve is biased to the closed configuration and is moved to the open configuration when the first fitting is operably engaged with the second fitting. In one preferred embodiment, the valve includes a hollow body defining a fluid passageway therethrough, and a resilient valve disc positioned in the fluid passageway of the body. The disc is biased into a closed configuration, wherein the disc blocks fluid flow through the fluid pathway, and the disc is movable to an open configuration, wherein fluid flow is permitted through the fluid pathway.

Further, the valve includes a support element positioned on the valve body for supporting the valve disc at the center of the disc, and at east one protrusion formed on the body for contacting the disc in the open configuration. Also, the valve has a retainer element that is positioned in the valve on the opposite side of the disc from the support element, to hold the center of the disc against the support element.

Additionally, the valve has a valve element reciprocally disposed in the fluid passageway of the valve on the same side of the disc as the retainer element. The valve element is movable between a first position, wherein the valve element is distanced from the valve disc, and a second position, wherein the valve element contacts the valve disc to move the disc into its open configuration, and the valve element is moved to its second position when the first fitting is engaged with second fitting.

When the luer fitting of the spike is configured as a male luer fitting, the valve element has a proximal portion extending beyond the valve body and configured to engage an inside surface of a female luer fitting.

In another aspect of the present invention, a device is disclosed for establishing a pathway for fluid communication from an IV bag. The device of the present invention includes a spike having a pointed distal end configured for puncturing the bag and a proximal end. Also, the device includes a luer fitting which is operably engaged with the proximal end of the spike.

In still another aspect of the present invention, a method is disclosed for establishing fluid communication between an intravenous (IV) component having a luer fitting and a fluid source having a puncturable membrane. The method of the present invention includes the steps of providing a spike and operably associating a luer fitting with the spike. The spike is then engaged with the fluid source by advancing the spike through the membrane of the fluid source, and the luer fitting of the spike is engaged with the luer fitting of the IV component to thereby establish fluid communication, between the fluid source and the IV component.

The details of the present invention, both as to its construction and operation, can best be understood in reference to the accompanying drawings, in which like numerals refer to like parts, and which:

DETAILED DESCRIPTION OF THE PREFERRED EMBODIMENT

Figure 1:
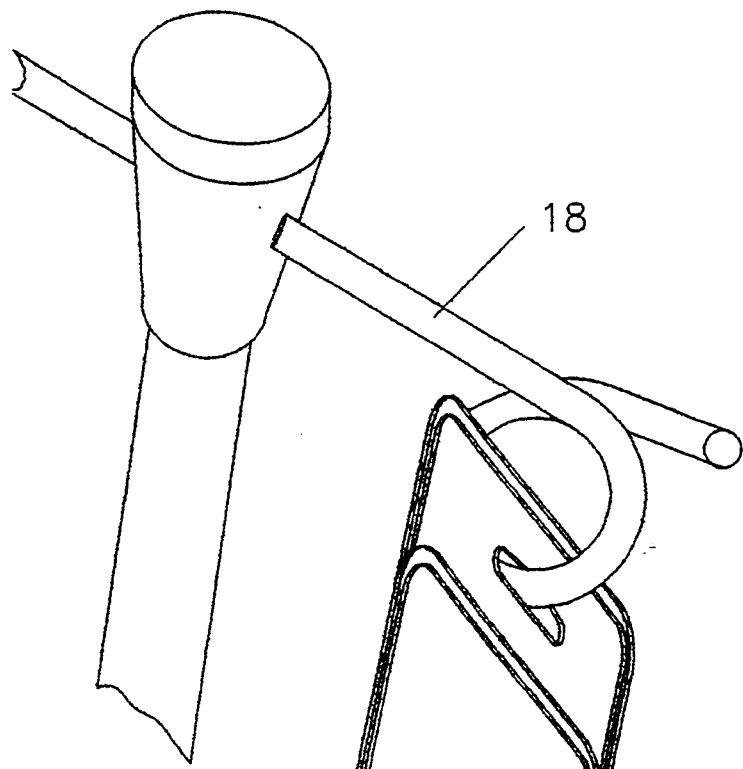
FIG. 1 is a perspective view of the spike of the present invention, in one intended environment.
Figure 1:
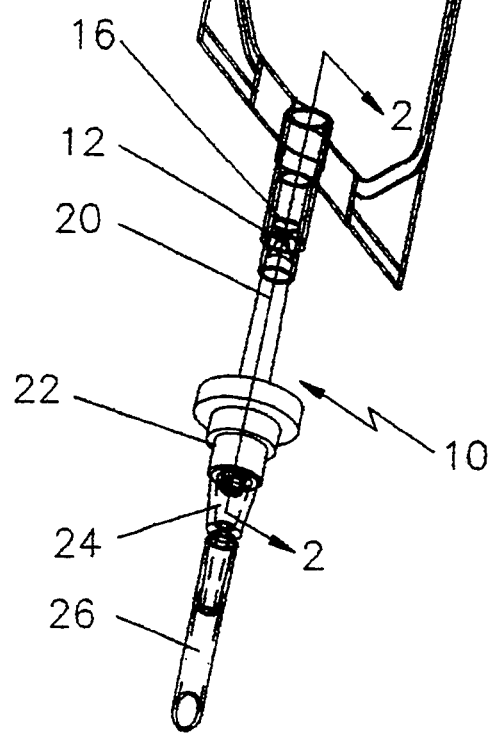

Referring initially to FIG. 1, a hollow rigid plastic spike is shown, generally designated 10. Preferably, the spike 10 is made of polypropylene, polyethylene, or other suitable biocompatible plastic material. As shown, the spike 10 has a pointed distal end 12 which can be operably engaged with a plastic single- or multi-ply bag 14 that holds IV fluid medicament or other biotechnology medium, e.g., cell culture.

More specifically, the pointed distal end 12 of the spike 10 is configured for puncturing a puncturable membrane 16 of the IV bag 14. It is to be understood that the membrane 16 can be positioned on the IV bag 14 in any one of a plurality of arrangements well-known in the art, e.g., the so-called "boat wedge" configuration. Accordingly, the pointed distal end 12 of the spike 10 is configured as the pointed distal end of a conventional spike. As shown in FIG. 1, the bag 14 can advantageously be suspended from a standard IV pole 18.

As further shown in FIG. 1, a fitting 22 is operably associated with a proximal end 20 of the spike 10. Preferably, the fitting 22 is a luer fitting that is formed on the spike 10 during manufacturing. As shown in FIG. 1, the fitting 22 of the spike 10 can be operably engaged with a complementarily-shaped luer fitting 24 of an IV component 26. While FIG. 1 shows that the IV component 26 can be an IV fluid line, it is to be understood that the component 26 can be other types of IV set components, such as a drip chamber or connector, which have an appropriately configured luer fitting.

Figure 2:
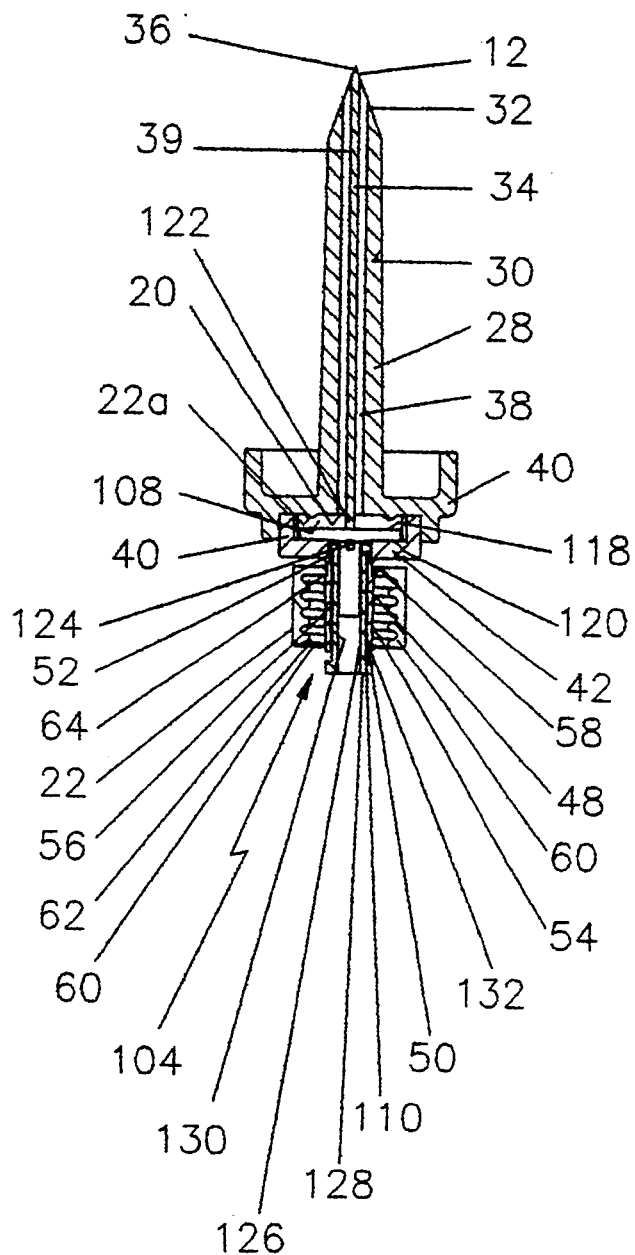
FIG. 2 is a cross-sectional view of the spike shown in FIG. 1, as seen along the line 2—2 in FIG. 1, with the valve in the closed configuration.

Now referring to FIG. 2, the spike 10 includes a hollow rigid elongated spike segment 28 having a cylindrical wall 30. The wall 30 has a sharpened distal rim 32. As further shown, the spike segment 28 has a central elongated post 34 positioned in the segment 28 coaxially therewith, and the post 34 has a pointed tip 36. A first cylindrical fluid passageway 38 is established between the post 34 and the wall 30 of the spike segment 28, and a second cylindrical fluid passageway 39 is established between the post 34 and the wall 30 of the spike segment 28.

A first cylindrical flange 40 is formed proximally on the spike segment 28, and the first flange 40 closely surrounds a second cylindrical flange 42 that is part of the luer fitting 22 shown in FIGS. 1 and 2. The first and second flanges 40, 42 are bonded together by means well-known in the art, e.g., solvent bonding, rf sealing, heat staking, or sonic welding. Alternatively, the flanges 40, 42 may be formed integrally together. A tamper-resistant cap (not shown) can be engaged with the flanges 40, 42 by means well-known in the art.

In the embodiment shown, the fitting 22 is a male luer fitting. More particularly, the fitting 22 includes an annular male element 48 that has a dull, i.e., non-sharp distal end 50 and a fluid passageway 52 which, as more fully disclosed below, can be placed in fluid communication with the fluid passageways 38, 39 of the spike segment 28. As shown in FIG. 2, the male element 48 is positioned coaxially with the spike segment 28.

In further reference to FIG. 2, the male element 48 has an outside surface 54 which is frusto-conical in shape and an inside surface 56 which is cylindrical in shape. Preferably, the male element 48 is formed with a collar 58. An annular, generally cylindrical cap 60 is rotatably engaged with the male element 48, and the cap 60 is captured in the space established between the collar 58 of the male element 48 and the second flange 42. FIG. 2 shows that the cap 60 is substantially coaxial with the male element 48.

Importantly, the cap 60 has a threaded inner surface 62 which faces the male element 48 and which is spaced from the element 48 for threadably engaging a complementarily threaded surface of, for example, the female luer fitting 24 (FIGS. 1 and 3) which is operably associated with the IV line 26 by means well-known in the art.

As disclosed above, the cap 60 is rotatably engaged with the male element 48. In this embodiment, the cap 60 is formed with an annular lip 64 which protrudes inwardly from the threaded inner surface 62 of the cap 60 for abutting the collar 58 and preventing the lip 64 from moving distally past the collar 58.

Figure 3:
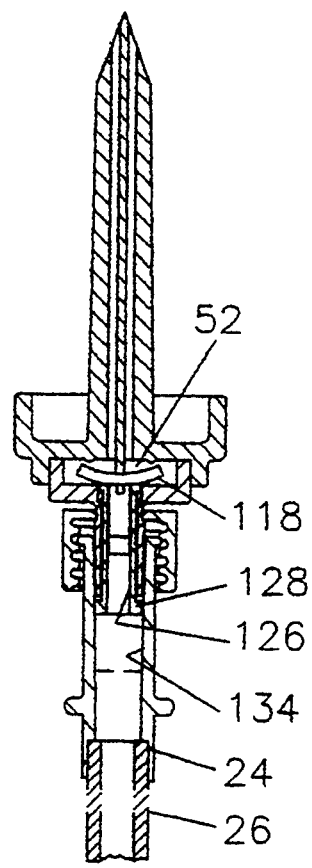
FIG. 3 is a cross-sectional view of the spike shown in FIG. 1, as would be seen along the line 2—2 in FIG. 1, with the valve in the open configuration.

In cross-reference to FIGS. 2 and 3, a male reflex valve, generally designated 104, is positioned in the fitting 22 for selectively permitting fluid communication through the fitting 22.

In one presently preferred embodiment the fitting 22 has a valve fluid inlet 108, a valve fluid outlet 110, and the fluid passageway 52 extends between the inlet 108 and outlet 110. A flexible resilient plastic or silicon rubber disc 118 is disposed in the fluid passageway 52. Specifically, the periphery of the plastic disc 118 rests on a seating surface 120 of the fitting 22 to establish a fluid-tight seal between the disc 118 and seating surface 120, when the disc 118 is in the closed configuration shown in FIG. 2. It is to be understood that the valve disc 118 is biased to the closed configuration shown in FIG. 2, wherein no fluid communication is permitted through the valve 104 (and, hence, through the fitting 22).

FIG. 2 shows that a support element 122 is formed on the post 34 of the spike segment 28 and extends across the fluid passageway 38 of the spike segment 28. As shown, the support element 122 supports the disc 118 in the center thereof. To this end, a slight depression may be formed in the center of the disc 118 to receive the support element 122 and thereby prevent side-to-side motion of the disc 118 relative to the support element 122. As further shown, the support element 122 is shaped as a cylinder, but it is to be understood that the support element 122 can have other suitable shapes, e.g., the support element 122 can have a triangular shape.

Additionally, a retainer element 124 is formed on fitting 22 and extends across the fluid passageway 52 of the fitting 22. As shown in FIG. 2, the retainer element 124 is positioned on the opposite side of the valve disc 118 from the support element 122. Accordingly, the retainer element 124 holds the center of the valve disc 118 against the support element 122.

Still referring to FIGS. 2 and 3, a rigid valve element 126 is shown slidably disposed in the fluid passageway 52 for reciprocal movement therein. As shown, the valve element 126 has an engagement member, preferably an annular head 128, and a skirt 130 that depends from the head 128. As further shown, the skirt 130 includes a plurality of, preferably two, legs, and has a cylindrical outer surface 132. FIG. 2 best shows that when the disc 118 is in the closed configuration, the head 128 of the valve element 126 protrudes distally beyond the fitting 22.

In cross-reference to FIGS. 2 and 3, the head 128 of the valve element 126 protrudes radially outwardly from the cylindrical outer surface 132 of the skirt 130. Accordingly, as best shown in FIG. 3, the head 128 can contact a tapered interior surface 134 of the female luer fitting 24 when the female luer fitting 24 is engaged with the male luer fitting 22. As the female luer fitting 24 is engaged with the male luer fitting 22, the valve element 126 is moved against the valve disc 118 to thereby deform the valve disc 118 into an open configuration, to permit fluid flow through the fluid passageway 38 of the spike segment 28 into the fluid passageway 52 of the male luer fitting 22.

Stated differently, when the valve element 126 is forced against the valve disc 118 by the female luer fitting 24, the skirt 130 of the valve element 126 contacts the surface of the disc 118. This deforms the valve disc 118, causing the sealing surface of the disc 118 to be distanced from the seating surface 120 of the male fitting 22, and thereby permitting fluid communication through the fluid passageway 52.

It is to be understood that when the female luer fitting 24 is disengaged from the male luer fitting 22, the resiliency of the valve disc 118 causes the disc 118 to resume its normally closed configuration, shown in FIG. 2.

Cylindrical or pyramidal protrusions 22a can be formed on the first flange 40 for preventing a vacuum lock between the disc 118 and the first flange 40. Alternatively, grooves (not shown) could be be formed in the first flange 40 for preventing a vacuum lock between the disc 118 and the first flange 40.

Figure 4:
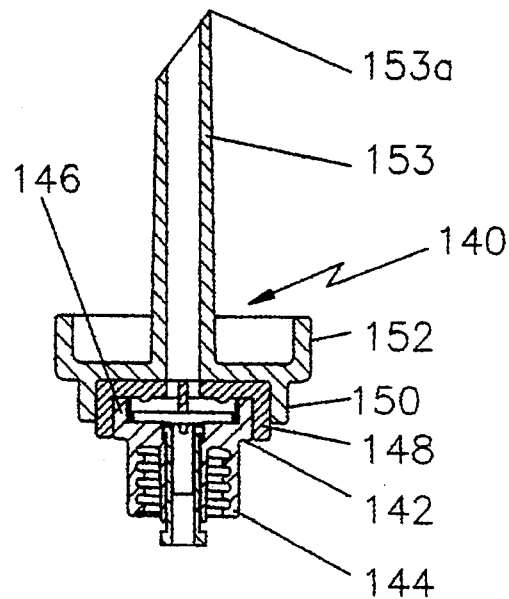
FIG. 4 is a cross-sectional view of an alternate embodiment of the spike of the present invention, as would be seen along the line 2—2 in FIG. 1.

Now referring to FIG. 4, in an .alternate embodiment of the spike of the present invention, generally designated 140, a male luer fitting 142 has a collar 144 formed integrally with a first flange 146. In turn, the first flange 146 is bonded to a connecting flange 148, and the connecting flange 148 is bonded to a second flange 150 of a spike segment 152. As shown, the spike segment 152 has an elongated hollow spike 153 that is formed with a bevelled distal end 153a for puncturing a membrane. The spike 140 is in all other essential respects identical to the spike 10 shown in FIGS. 1–3.

Figure 5:
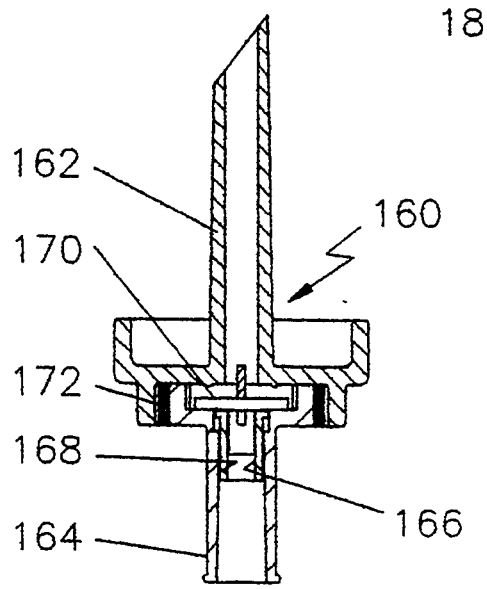
FIG. 5 is a cross-sectional view of another alternate embodiment of the spike of the present invention, as would be seen along the line 2—2 in FIG. 1.

FIG. 5 shows that in yet another alternate embodiment of the spike of the present invention, generally designated 160, a spike segment 162 is connected to a female luer fitting 164. A valve element 166 having a cylindrical outer surface 168 is reciprocally disposed in the luer fitting 164. In contrast to the valve element 126 shown in FIGS. 2 and 3, the valve element 166 shown in FIG. 5 has no head which protrudes radially outwardly from the surface 168 of the valve element 166.

Consequently, a male luer fitting (not shown) can be engaged with the female luer fitting 164. It is to be appreciated that the male luer fitting, once engaged with the female luer fitting 164, urges the valve element 166 against a valve disc 170 to deform the disc 170 to the open configuration. If desired, a cavity 172 having a threaded wall can be formed on the spike 160 for receiving a tamper-resistant cap (not shown) by means well-known in the art. The spike 160 is in all other essential respects identical to the spike 10 shown in FIGS. 1–3.

Figure 6:
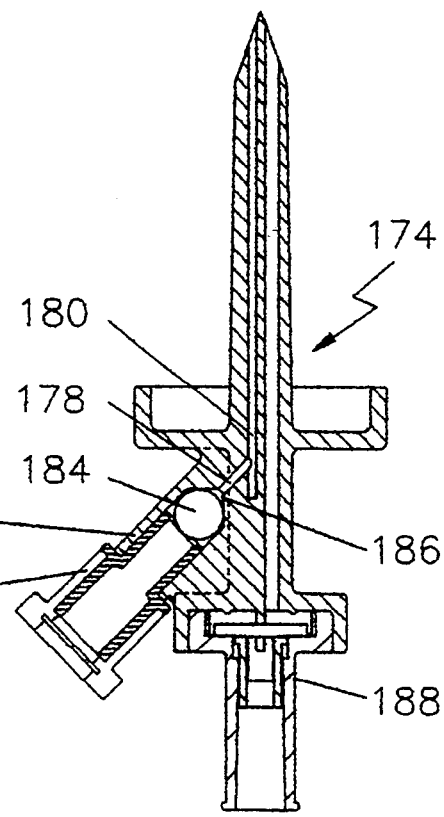
FIG. 6 is a cross-sectional view of still another alternate embodiment of the spike of the present invention, as would be seen along the line 2—2 in FIG. 1.

FIG. 6 shows a spike 174 which is a vented spike, i.e., the spike 174 has a gas tube 176 defining a gas passageway 178, and the gas passageway 178 is in fluid communication with a first fluid passageway 180 of the spike 174.

Preferably, a hydrophobic membrane 182 is positioned athwart the gas passageway 178, and a ball 184 is positioned for reciprocating movement within the gas passageway 178. The ball 184 can contact a seat 186 that is formed in the gas tube 176 to block fluid flow through the gas passageway 178. On the other hand, gas within the fluid passageway 180 will urge the ball 184 away from the seat 186 to permit the gas to pass out of the fluid passageway 180 through the gas passageway 178 and hydrophobic membrane 182. The spike 174 also has a female luer fitting with valve 188.

While tile particular spike as herein shown and described in detail is fully capable of attaining the: above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A spike assembly for establishing fluid flow to and from an IV fluid container having a membrane, comprising:

a hollow pointed puncturing element having a distal end configured for puncturing the membrane of the IV fluid container and an open proximal end, wherein the open proximal end is configured as a first luer fitting for engaging a complementarily-shaped second luer fitting; and a valve disposed in the proximal end of the puncturing element, the valve including a resilient valve member defining an outer periphery that is uninterrupted within the periphery and deformable to an open configuration, wherein a pathway for fluid communication is established around the periphery and through the spike when the second luer fitting is engaged with the first, the valve member being biased to a closed configuration, wherein a pathway for fluid communication is not established through the spike when the second luer fitting is not engaged with the first.

2. The spike of claim 1, wherein the distal end of the spike is pointed, and the spike defines two fluid pathways.

3. The spike of claim 1, wherein the distal end of the spike is bevelled, and the spike defines one fluid pathway.

4. The spike of claim 1, wherein the luer fitting is a male luer fitting, and the spike further comprises an annular cap engaged with the male luer fitting in a surrounding relationship therewith, the cap having a threaded inner surface facing the male luer fitting and spaced therefrom for threadably engaging a complementarily threaded surface.

5. The spike of claim 4, wherein the cap is rotatably engaged with the male luer fitting.

6. The spike of claim 4, wherein the cap is fixedly attached to the male luer fitting.

7. The spike of claim 1, wherein the valve is biased to the closed configuration and is moved to the open configuration when the first fitting is operably engaged with the second fitting.

8. The spike of claim 7, wherein the valve includes:
a hollow body defining a fluid passageway therethrough; and wherein
the valve member includes a resilient valve disc positioned in the fluid passageway of the body and being biased into a closed configuration, wherein the disc blocks fluid flow through the fluid passageway, the disc being movable to an open configuration, wherein fluid flow is permitted through the fluid passageway, the valve disc defining a continuous surface and a periphery circumscribing the surface such that fluid communication through the surface of the disc is prevented in the open and closed configurations.

9. The spike of claim 8, further comprising a gas tube defining a gas passageway, the gas passageway being in fluid communication with the fluid passageway.

10. The spike of claim 8, wherein the valve body is bonded to the puncturing element.

11. The spike of claim 8, wherein the valve further comprises:
a support element positioned on the valve body for supporting the valve disc at the center of the disc;
at least one protrusion formed on the body for contacting the disc in the open configuration;
a retainer element positioned in the valve on the opposite side of the disc from the support element, to hold the center of the disc against the support element; and a valve element reciprocally disposed in the fluid passageway of the valve on the same side of the disc as the retainer element, the valve element being movable between a first position, wherein the valve element is distanced from the valve disc, and a second position, wherein the valve element contacts the valve disc to move the disc into its open configuration, wherein the valve element is moved to its second position when the first fitting is engaged with second fitting.

12. The spike of claim 11, wherein the valve element has a proximal portion extending beyond the valve body and configured to engage an inside surface of a female luer fitting.

13. A device, comprising:
an IV container;
a spike having a distal end configured for puncturing the IV container, the spike also having a proximal end;
a luer fitting operably engaged with the proximal end of the spike, the luer fitting establishing a fluid passageway; and
a valve including a seating surface and a valve member defining an outer periphery that is uninterrupted within the periphery and biased against the seating surface, the valve being disposed in the passageway of the luer fitting to selectively permit fluid communication through the passageway when the periphery of the valve member is distanced from the seating surface.

14. The device of claim 13, wherein the luer fitting of the device is a male luer fitting.

15. The device of claim 13, wherein the luer fitting of the device is a female luer fitting.

16. The device of claim 13, wherein the distal end of the spike is pointed, and the spike defines two fluid pathways.

17. The device of claim 13, wherein the distal end of the spike is bevelled, and the spike defines one fluid pathway.

18. The device of claim 13, wherein the valve has a closed configuration and an open configuration, and the valve is biased to the closed configuration and is moved to the open configuration when the luer fitting of the device is operably engaged with a complementarily-shaped luer fitting.

19. The device of claim 18, wherein the valve includes:
a hollow body defining a fluid passageway therethrough; and
the valve member is a resilient valve disc positioned in the fluid passageway of the body and being biased into a closed configuration, wherein the disc blocks fluid flow through the fluid passageway, the disc being movable to an open configuration, wherein fluid flow is permitted through the fluid passageway, the valve disc defining a continuous surface and a periphery circumscribing the surface such that fluid communication through the surface of the disc is prevented in the open and closed configuration.

20. The device of claim 19, further comprising a gas tube defining a gas passageway, the gas passageway being in fluid communication with the fluid passageway of the valve body.

21. The device of claim 19, wherein the valve body is bonded to the spike.

22. The device of claim 19, wherein the valve further comprises:
- a support element positioned on the valve body for supporting the valve disc at the center of the disc;
- at least one protrusion formed on the body for contacting the disc in the open configuration;
- a retainer element positioned in the valve on the opposite side of the disc from the support element, to hold the center of the disc against the support element; and
- a valve element reciprocally disposed in the fluid passageway of the valve on the same side of the disc as the retainer element, the valve element being movable between a first position, wherein the valve element is distanced from the valve disc, and a second position, wherein the valve element contacts the valve disc to move the disc into its open configuration, wherein the valve element is moved to its second position when the luer fitting of the device is engaged with a complementarily-shaped luer fitting.

23. The device of claim 22, wherein the valve element has a proximal portion extending beyond the valve body and configured to engage an inside surface of a female luer fitting.

24. A method for establishing fluid communication between an intravenous (IV) component having a luer fitting and art IV container having a puncturable membrane, comprising the steps of:
- (a) providing a pointed spike;
- (b) connecting a luer fitting to the spike;
- (c) positioning a valve including a valve member defining an outer periphery that is uninterrupted within the periphery in the spike to selectively permit fluid flow through the spike;
- (d) engaging the spike with the IV connector by advancing the spike through the membrane; and
- (e) engaging the luer fitting of the spike with the luer fitting of the IV component to deform the valve member to permit fluid communication around the periphery therof and thereby establish fluid communication between the IV container and the IV component.

* * * * *